US010253166B2

(12) United States Patent
Wertz et al.

(10) Patent No.: US 10,253,166 B2
(45) Date of Patent: Apr. 9, 2019

(54) FLAME-RETARDANT MICROCAPSULE CONTAINING CYCLIC PHOSPHAZENE

(71) Applicant: International Business Machines Corporation, Armonk, NY (US)

(72) Inventors: Jason T. Wertz, Pleasant Valley, NY (US); Brandon M. Kobilka, Tucson, AZ (US); Jacob T. Porter, Highland, NY (US); Joseph Kuczynski, North Port, FL (US)

(73) Assignee: International Business Machines Corporation, Armonk, NY (US)

( * ) Notice: Subject to any disclaimer, the term of this patent is extended or adjusted under 35 U.S.C. 154(b) by 16 days.

(21) Appl. No.: 15/697,596

(22) Filed: Sep. 7, 2017

(65) Prior Publication Data

US 2019/0071557 A1 Mar. 7, 2019

(51) Int. Cl.
*C08K 5/5399* (2006.01)
*C08G 79/025* (2016.01)
*C07F 9/22* (2006.01)
*C07F 9/6521* (2006.01)

(52) U.S. Cl.
CPC ............ *C08K 5/5399* (2013.01); *C07F 9/222* (2013.01); *C07F 9/6521* (2013.01); *C08G 79/025* (2013.01)

(58) Field of Classification Search
CPC ...... C08K 5/5399; C07F 9/222; C08G 79/025
USPC ....................................................... 524/116
See application file for complete search history.

(56) References Cited

U.S. PATENT DOCUMENTS

| | | | |
|---|---|---|---|
| 6,876,125 | B2 | 4/2005 | Basheer et al. |
| 7,935,410 | B2 | 5/2011 | Orologio |
| 9,499,695 | B2 | 11/2016 | Tomita et al. |
| 2008/0248126 | A1 | 10/2008 | Cheng et al. |
| 2009/0078918 | A1 | 3/2009 | Huettner et al. |
| 2009/0110738 | A1 | 4/2009 | Gordy et al. |
| 2010/0087115 | A1 | 4/2010 | Davis et al. |
| 2010/0285313 | A1 | 11/2010 | Zhang et al. |
| 2010/0311900 | A1 | 12/2010 | Lang et al. |
| 2011/0131700 | A1 | 6/2011 | Tsui et al. |
| 2013/0266661 | A1 | 10/2013 | Sohn et al. |
| 2013/0338280 | A1 | 12/2013 | Boday et al. |

FOREIGN PATENT DOCUMENTS

| | | |
|---|---|---|
| JP | 2003342408 A | 12/2003 |
| JP | 2006137862 A | 6/2006 |
| WO | 2009058147 A1 | 5/2009 |

OTHER PUBLICATIONS

Allcock, "Polyphosphazene elastomers, gels, and other soft materials," Soft Matter, Accepted May 28, 2012, 13 pages, DOI: 10.1039/c2sm26011e.

Allcock et al., "Synthesis and Structure of Small-Molecule Cyclic Phosphazenes Bearing Ortho-Substituted Aryloxy and Phenoxy Substituents," Pennsylvania State University Department of Chemistry Contribution, Inorganic Chemistry, vol. 31, No. 13, 6 pages.

Allcock et al., "Synthesis of New Polyphosphazene Elastomers," Macromolecules, American Chemical Society, vol. 23, No. 17, Aug. 20, 1990, 5 pages.

Amin et al., "Recent Research Progress in the Synthesis of Polyphosphazene Elastomers and Their Applications," Polymer-Plastics Technology and Engineering, 2010, 7 pages, DOI: 10.1080/03602559.2010.496387.

Hu et al., "A facile method to prepare UV light-triggered self-healing polyphosphazenes," Springer Science+Business Media, Published Dec. 24, 2014, 9 pages, DOI: 10.1007/s10853-014-8786-y.

Krishnadevi et al., "Development of halogen-free flame retardant phosphazene and rise husk ash incorporated benzoxazine blended epoxy composites for microelectronic applications," Royal Society of Chemistry, Accepted Jun. 17, 2015, 13 pages, DOI: 10.1039/c5nj00364d.

Modzelewski et al., "Elastomeric Polyphosphazenes with Phenoxy-Cyclotriphosphazene Side Groups," Macromolecules, 2015, 7 pages, DOI: 10.1021/acs.macromol.5b1892.

Modzelewski et al., "Polyphosphazene Elastomers Containing Interdigitated Oligo-p-phenyleneoxy Side Groups: Synthesis, Mechanical Properties, and X-ray Scattering Studies," Macromolecules, Published Jul. 17, 2015, 9 pages, DOI: 10.1021/acs.macromol.5bo1191.

Rothemund et al., "Preparation of polyphosphazenes: a tutorial review," Royal Society of Chemistry, Apr. 27, 2016, 16 pages, DOI: 10.1039/c6cs00340k.

Singler et al., "Phosphazene Elastromers, Synthesis, Properties, and Applications," American Chemical Society, Aug. 29, 1984, 15 pages, DOI: 10.1021/bk-1984-0260.ch009.

Wilfert et al., "Water-Soluble, Biocompatible Polyphophazenes with Controllable and pH-Promoted Degradation Behavior," Journal of Polymer Science, Nov. 22, 2013, 8 pages, DOI: 10.1002/pola.27002.

Brown et al., "In situ poly(urea-formaldehyde) microencapsulation of dicyclopentadiene," Taylor & Francis Health Sciences, Nov.-Dec. 2003, vol. 20, No. 6, 12 pages, DOI: 10.1080/02652040310001541609.

Unknown, "Fire Retardant Microcapsules for Incorporation Into Circuit Boards," An IP.com Prior Art Database Technical Disclosure, Electronic Publication Date Aug. 16, 2011, 4 pages, IP.com No. IPCOM000209808D.

(Continued)

Primary Examiner — Hannah J Pak
(74) Attorney, Agent, or Firm — Peter Edwards

(57) ABSTRACT

A flame-retardant microcapsule with a shell containing a cyclic phosphazene molecule, a process for forming a flame-retardant microcapsule with a shell containing a cyclic phosphazene molecule, and an article of manufacture including a flame-retardant microcapsule with a shell containing a cyclic phosphazene molecule are disclosed. The process for forming the flame-retardant microcapsule with the shell containing the cyclic phosphazene molecule may include providing a cyclic phosphazene molecule, forming an aqueous mixture containing the cyclic phosphazene molecule, adding a payload agent into the aqueous mixture, and adding a curing agent into the aqueous mixture.

20 Claims, 7 Drawing Sheets

(56) References Cited

OTHER PUBLICATIONS

Unknown, "Microcapsules With Inherent Flame Retardancy," An IP.com Prior Art Database Technical Disclosure, Electronic Publication Date Jun. 7, 2012, 3 pages, IP.com No. IPCOM000218847D.
Unknown, "Flame Retardant Bubble Wrap," Protec, printed Aug. 31, 2017, 8 pages https://www.protection.co.uk/products/flame-retardant-bubble-wrap/.

200

210

M = ----- O—L
      215

L =   R    or      or   
      220
                    225                      230

X =   R    or  ----- OH   or  ----- NH₂
      220        240              245

R =   H   or  HC≡CH  or  H₂C═CHCH₂  or  $C_3H_6O$  or  $C_4H_6O_2$  or  $C_9H_8O_2$  or  $C_3H_4O_2$
220   250     255          260             265          270             275             280

FLAME-RETARDANT MICROCAPSULE CONTAINING CYCLIC PHOSPHAZENE

BACKGROUND

The present disclosure relates to flame-retardant microcapsules and, more specifically, flame-retardant microcapsules with a shell containing a cyclic phosphazene molecule.

SUMMARY

Various embodiments are directed to flame-retardant microcapsules with a shell containing a cyclic phosphazene molecule. Additional embodiments are directed to a process of forming a flame-retardant microcapsule with a shell containing a cyclic phosphazene molecule. The process may include providing the cyclic phosphazene molecule, forming an aqueous mixture containing the cyclic phosphazene molecule, adding a payload agent into the aqueous mixture, and adding a curing agent into the aqueous mixture. Providing the cyclic phosphazene molecule may include functionalizing an unfunctionalized cyclic phosphazene molecule. Functionalizing the unfunctionalized cyclic phosphazene molecule may be a reaction including at least one of functionalized aryl alcohols and functionalized aliphatic alcohols. The process of forming the flame-retardant microcapsule may further include adding one or more solvents into the aqueous mixture, the one or more solvents including at least one of aprotic solvents and protic solvents. Further embodiments are directed to an article of manufacture comprising a flame-retardant microcapsule with a shell containing a cyclic phosphazene molecule. The shell containing the cyclic phosphazene molecule may be covalently bound into a polymeric matrix.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
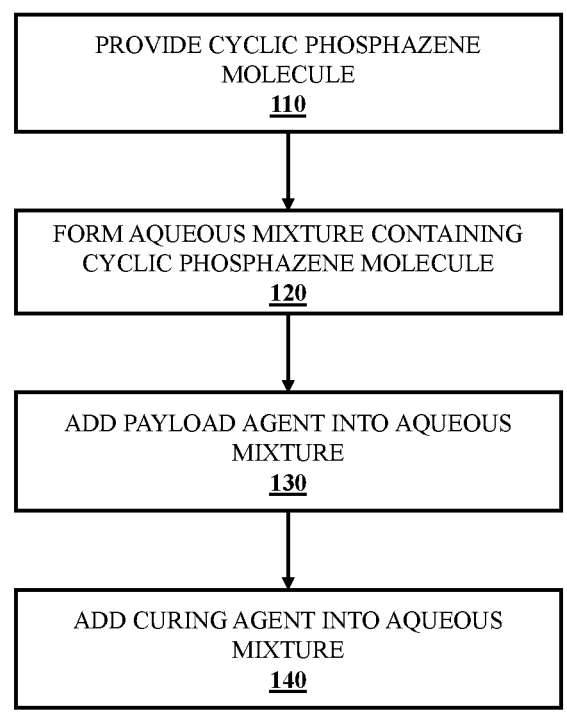
FIG. 1 depicts a flowchart of a process of forming a flame-retardant microcapsule with a shell containing a cyclic phosphazene molecule, according to various embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure relates to flame-retardant microcapsules and, more specifically, flame-retardant microcapsules with a shell containing cyclic phosphazene. While the present disclosure is not necessarily limited to such applications, various aspects of the disclosure may be appreciated through a discussion of various examples using this context.

Microcapsules are widely used as release systems containing payloads such as self-healing agents, disinfectants, repellants (e.g., fluid, insect, or any type of repellant), or any other substances. The rupture and eventual release of the payload is dependent on mechanically breaking the polymer shell, which may be done through scratching, puncturing, or other mechanical means applied to the polymer surface.

The present disclosure provides a flame-retardant microcapsule that contains cyclic phosphazene functionalities within the shell of the capsule. The cyclic phosphazene may incorporate orthogonal functionalities that can covalently bind into a polymer matrix, allowing for more sensitive detection of cracks in the matrix. Orthogonal functionalities may be functional groups orthogonal to the shell. Phosphazenes are flame retardant, therefore adding cyclic phosphazene molecules within the shell of the microcapsule may incorporate a flame-retardancy to the microcapsule. By incorporating cyclic phosphazene molecules into the shell of the microcapsule, a number of additives needed to create the microcapsule may be reduced. When forming a general microcapsule, the microcapsule may be mixed with a polymer and then, in a second step, mixed with a flame-retardant molecule. When forming a microcapsule containing a cyclic phosphazene molecule, the cyclic phosphazene molecule may be both the polymer and the flame-retardant molecule, therefore reducing the number of additives. In some embodiments, the microcapsule containing the cyclic phosphazene moieties in the shell wall binds directly into the polymer matrix. The microcapsule may also deliver a payload. In some embodiments, the flame-retardant microcapsule may be blended or chemically reacted with a polymer. Examples of polymers can include epoxies, polyhydroxyurethanes, polycarbonates, polyesters, polyacrylates, polyimides, polyamides, polyureas, poly(vinyl-esters), etc. In various embodiments, the microcapsules are generated with homogenous size distributions that may not leach out the contained payload. Further, the homogeneous size distributions of the microcapsules may bind directly into a polymer matrix, and can be utilized as a functional filler to strengthen the composite.

Flame-retardants are used within polymers, textiles, coatings, and other substances to limit the spread of a fire. These flame-retardants come in different states, including powders, liquids, etc., depending on their application. Flame-retardants may have broad size distributions which may hinder the manufacturing of products by changing the flow properties. The inclusion of cyclic phosphazene in the flame-retardant microcapsule may allow for the microcapsule to be prepared in a tight distribution of diameters by, for example, controlling a mixer speed, resulting in a near uniform distribution. With a near uniform distribution, agglomeration and clumping are minimized.

The microcapsules may be manufactured using an oil-in-water emulsion technique to create a protective flame retardant polymeric shell around a payload agent core. The cyclic phosphazene molecules may replace, or be used in combination with, standard resorcinol in the microcapsule synthesis. In some embodiments, the cyclic phosphazene molecules are formed, or generated, to become a new resorcinol-like monomer. The cyclic phosphazene molecules may include an orthogonal functionality.

Figure 2:
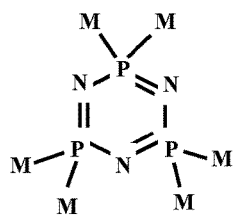
FIG. 2 depicts a diagrammatic representation of a molecular structure of a cyclic phosphazene molecule, according to various embodiments.
Figure 2:
Figure 2:
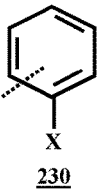
Figure 4:
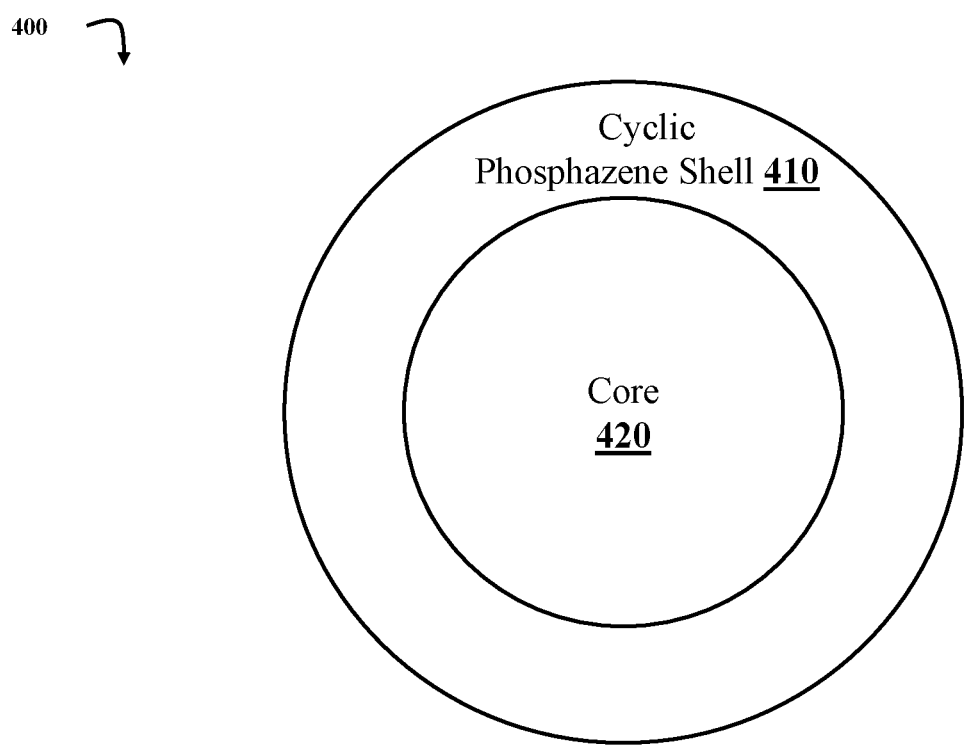
FIG. 4 depicts a schematic diagram of a microcapsule with a cyclic phosphazene shell, according to various embodiments.

Referring now to FIG. 1, a flowchart illustrating a process 100 of forming a flame-retardant microcapsule with a shell containing cyclic phosphazene molecules is depicted, according to various embodiments. In an embodiment, the flame-retardant microcapsule with the shell containing a cyclic phosphazene molecule is flame-retardant microcapsule 400 (FIG. 4). In some embodiments, the cyclic phosphazene molecule is cyclic phosphazene molecule 210 (FIG. 2).

In various embodiments, process 100 begins with operation 110 to provide a functionalized cyclic phosphazene molecule. In some embodiments, providing the cyclic phosphazene molecule includes functionalizing a cyclic phosphazene molecule. Functionalizing the cyclic phosphazene molecule adds functional groups (i.e., moieties that contribute to a compound's reactivity) to the molecule. Functionalizing the cyclic phosphazene molecule may be a reaction including at least one of functionalized aryl alcohols and functionalized aliphatic alcohols. Functionalizing the unfunctionalized cyclic phosphazene molecule is further discussed herein.

In various embodiments, process 100 continues with operation 120 to form an aqueous mixture containing the cyclic phosphazene molecule. In some embodiments, forming the aqueous mixture containing the cyclic phosphazene molecule includes adding the cyclic phosphazene molecule to a pre-formed aqueous mixture. The aqueous mixture may include one or more solvents, with at least one solvent being water. In some embodiments, forming the aqueous mixture containing the cyclic phosphazene molecule includes mixing a plurality of molecules including at least water and the cyclic phosphazene molecules.

In various embodiments, process 100 continues with operation 130 to add a payload agent into the aqueous mixture. The payload agent acts as an emulsifying agent (e.g., emulsifier) and is added, or disbursed, into the aqueous mixture to begin the emulsion process. In various embodiments, the payload agent is the core of the microcapsule. The payload agent may act as the oil phase in an oil-in-water emulsion technique. In some embodiments, the payload agent is a latent curing agent (e.g., N-ethylpiperazine), where the latent curing agent assists in curing, or hardening, a surface (e.g., forming the core of the microcapsule). In various embodiments, the payload agent is a polymerizable molecule such as cyclic olefins, norbornene, substituted norbornene, cyclooctadiene, substituted cyclooctadiene, lactones, acrylates, acrylic acids, styrenes, isoprene, butadiene, and/or epoxies. The payload agent may require an activator such as a catalyst and/or initiator, which may be chosen by those skilled in the art. In various embodiments, the payload agent is added with additional ingredients such as other monomers and/or prepolymers, stabilizers, solvents, viscosity modifiers, odorants, colorant and dyes, blowing agents, antioxidants, and co-catalysts. In some embodiments, solvents are added into the aqueous mixture to incorporate the solvents into the flame-retardant microcapsule. The solvents may be aprotic solvents, protic solvents, or a mixture of both aprotic and protic solvents.

In various embodiments, a cross-linking agent is added into the aqueous mixture to generate a shell around the payload agent, the shell containing the cyclic phosphazene molecule. The cross-linking agent may react with the payload agent or a separate emulsifying agent in order to generate, or form, the shell. The emulsifying agent may be a self-healing agent. In some embodiments, the separate emulsifying agent is added to the aqueous mixture before the cross-linking agent is added. In various embodiments, the separate emulsifying agent is added to the aqueous mixture concurrently with adding the cross-linking agent. The separate emulsifying agent may be added to the aqueous mixture subsequently to adding the cross-linking agent.

In various embodiments, process 100 continues with operation 140 to add a curing agent into the aqueous mixture. Adding the curing agent may complete the reaction and form the microcapsule with the shell containing the cyclic phosphazene molecule. The curing agent is a molecule that, when added into the aqueous mixture, reacts and hardens the shell around the microcapsule. In some embodiments, the curing agent hardens the shell by facilitating, or assisting, in the bonding of the molecules within the shell. This may include facilitating the bonding between cyclic phosphazene molecules. In various embodiments, the cyclic phosphazene molecules within the shell have orthogonal functionality, which may help strengthen bonds within the shell. The orthogonal functionality of the cyclic phosphazene molecules may result in covalent bonding between the cyclic phosphazene molecules, thus covalently binding into a polymeric matrix. Covalently binding into the polymeric matrix may allow for an increased sensitivity for detection of cracks in the matrix. After the formation of the microcapsule with the shell containing cyclic phosphazene molecules, the microcapsule may be washed and sieved to remove any unreacted material.

In various embodiments, process 100 includes continuously stirring the aqueous mixture for each operation 110, 120, 130, and 140. The stir speed of the aqueous mixture may be changed or adjusted in order to adjust the size of the microcapsule. An increased stir speed of the aqueous mixture encourages a finer emulsion, and therefore a decrease in size, or diameter, of the microcapsule. A decreased stir speed may result in an increase in size, or diameter, of the microcapsule. In some embodiments, the microcapsule containing the cyclic phosphazene molecules is utilized as a functional filler to strengthen a composite. In various embodiments, process 100 is a stepwise reaction. A stepwise reaction may involve two or more consecutive reactions. In some embodiments, process 100 is a single reaction.

Referring to FIG. 2, a diagrammatic representation 200 illustrating a molecular structure of generic cyclic phosphazene molecule 210 and sample substituents is depicted, according to various embodiments. In various embodiments, cyclic phosphazene molecule 210 has orthogonal functionality. The orthogonal functionality may allow for the cyclic phosphazene molecule 210 to be covalently bonded into a polymeric matrix. Each M of cyclic phosphazene molecule 210 is a first variable substituent, in some embodiments. In various embodiments, the first variable substituent M is substituent 215. Each L of substituent 215 may be a second variable substituent. The dashed line in FIG. 2 can indicate a bond location. Examples of second substituent L include a third variable substituent R 220, a phenyl substituent 225, and a substituted-phenyl substituent 230 bonded to a fourth variable substituent X. In some embodiments, the dashed line through the phenyl ring of substituent 225 and substituent 230 indicates that the bond location may be at any carbon in the phenyl ring. Examples of fourth variable substituent X include third variable substituent R 220, a hydroxide molecule 240, and an amidogen molecule 245. Examples of third variable substituent R 220 include a hydrogen molecule 250, a substituent including a vinyl group 255, a substituent including an allyl group 260, and a substituent including an epoxy group 265. Additional examples of third variable substituent R may include a substituent including an acrylate group 270, a substituent including phenyl acrylic acid 275, and a substituent including acryloyl acid 280. It should be understood that these molecular structures and substituents are only examples, and other molecules can be used in cyclic phosphazene molecules.

Figure 3A:
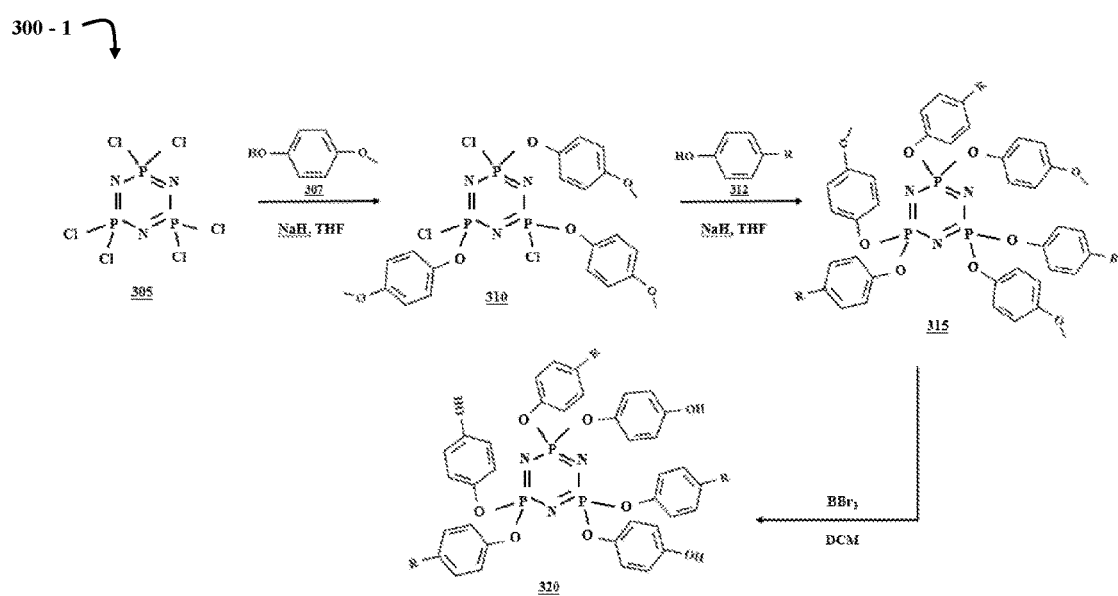
FIG. 3A depicts a first chemical reaction diagram illustrating a process of forming a cyclic phosphazene molecule, according to various embodiments.

Referring to FIG. 3A, a chemical reaction diagram illustrating a sample process 300-1 of forming a cyclic phosphazene molecule is depicted, according to various embodiments. In various embodiments, process 300-1 of forming the cyclic phosphazene molecule includes functionalizing a cyclic phosphazene molecule. Process 300-1 is one possible reaction for functionalizing a cyclic phosphazene molecule, and is illustrated for example purposes.

Process 300-1 begins with an exemplary cyclic phosphazene molecule 305. In some embodiments, cyclic phosphazene molecule 305 is an unfunctionalized cyclic phosphazene molecule. A strong base, such as sodium hydride (NaH), and tetrahydrofuran (THF) may be reacted with cyclic phosphazene molecule 305. In various embodiments, other bases (e.g., potassium hydride, lithium hydride, rubidium hydride, cesium hydride, etc.) or acids may be used in place of the strong base NaH. Additionally, a molecule such as phenol molecule 307 may be reacted with the cyclic phosphazene molecule 305, NaH, and THF to form cyclic phosphazene molecule 310.

Cyclic phosphazene molecule 310 may then be reacted with NaH, THF, and a phenol molecule such as phenol molecule 312 to form cyclic phosphazene molecule 315. In various embodiments, the phenol molecules 307 and 312 include functional groups to functionalize the unfunctionalized cyclic phosphazene molecule 305. In various embodiments, cyclic phosphazene molecule 315 is reacted with a strong Lewis acid (e.g., boron tribromide) and a solvent (e.g., dichloromethane (DCM)) to form functionalized phosphazene molecule 320. In some embodiments, substituent R in process 300-1 is the third variable substituent R (FIG. 2).

Figure 3B:
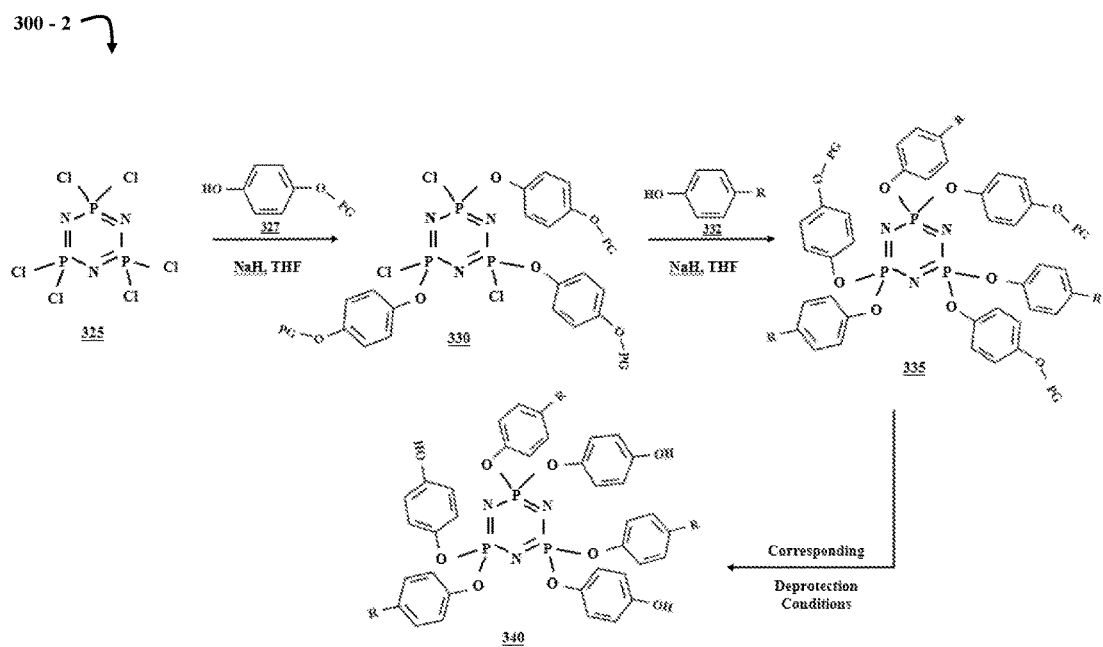
FIG. 3B depicts a second chemical reaction diagram illustrating a process of forming a cyclic phosphazene molecule, according to various embodiments.

Referring to FIG. 3B, a chemical reaction diagram illustrating a sample process 300-2 of forming a cyclic phosphazene molecule is depicted, according to various embodiments. In various embodiments, process 300-2 of forming the cyclic phosphazene molecule includes functionalizing a cyclic phosphazene molecule. Process 300-2 is one possible reaction for functionalizing a cyclic phosphazene molecule, and is illustrated for example purposes.

Process 300-2 begins with an exemplary cyclic phosphazene molecule 325. In some embodiments, cyclic phosphazene molecule 325 is an unfunctionalized cyclic phosphazene molecule. A strong base, such as sodium hydride (NaH), and tetrahydrofuran (THF) may be reacted with cyclic phosphazene molecule 325. In various embodiments, other bases (e.g., potassium hydride, lithium hydride, rubidium hydride, cesium hydride, etc.) or acids may be used in place of the strong base NaH. Additionally, a molecule such as phenol molecule 327, with a protecting group (PG), may be reacted with the cyclic phosphazene molecule 325, NaH, and THF to form cyclic phosphazene molecule 330. Protecting groups may protect portions of the cyclic phosphazene molecule that may not sustain the addition of the necessary reagents for the formation of the functionalized cyclic phosphazene molecule. Examples of protecting groups may include trimethylsilyl (TMS), triethylsilyl (TES), tert-butyldiphenylsilyl (TBS), triisopropylsilyl (TIPS), methoxymethyl ether (MOM), and tetrahydropyranyl (THP) groups.

Cyclic phosphazene molecule 330 may then be reacted with NaH, THF, and a phenol molecule such as phenol molecule 332 to form cyclic phosphazene molecule 335. In various embodiments, the phenol molecules 327 and 332 include functional groups to functionalize the unfunctionalized cyclic phosphazene molecule 325.

In various embodiments, cyclic phosphazene molecule 335 is then deprotected to form functionalized phosphazene molecule 340. Deprotecting cyclic phosphazene molecule 335 can include removing the protecting groups (PG). The reaction conditions under which the protecting groups are removed can vary. For example, silyl protecting groups (e.g., TMS, TES, TBS, and TIPS) can be removed by a reaction with fluorides, such as tetrabutylammonium fluoride (TMF). The silyl protecting groups, as well as other protecting groups (e.g., MOM and THP) can also be removed by acids and bases. In some embodiments, substituent R in process 300-2 is the third variable substituent R (FIG. 2).

Figure 3C:
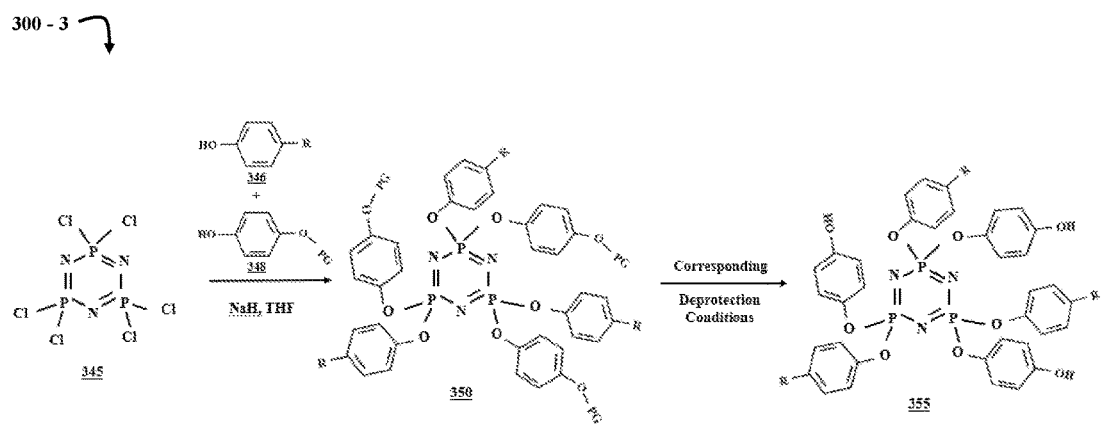
FIG. 3C depicts a third chemical reaction diagram illustrating a process of forming a cyclic phosphazene molecule, according to various embodiments.

Referring to FIG. 3C, a chemical reaction diagram illustrating a sample process 300-3 of forming a cyclic phosphazene molecule is depicted, according to various embodiments. In various embodiments, process 300-3 of forming a cyclic phosphazene molecule includes functionalizing a cyclic phosphazene molecule. Process 300-3 is one possible reaction for functionalizing a cyclic phosphazene molecule, and is illustrated for example purposes.

Process 300-3 begins with an exemplary cyclic phosphazene molecule 345. In some embodiments, cyclic phosphazene molecule 345 is an unfunctionalized cyclic phosphazene molecule. A strong base, such as sodium hydride (NaH), and tetrahydrofuran (THF) may be reacted with cyclic phosphazene molecule 345. In various embodiments, other bases (e.g., potassium hydride, lithium hydride, rubidium hydride, cesium hydride, etc.) or acids may be used in place of the strong base NaH. Additionally, the NaH, THF, and the cyclic phosphazene molecule 345 may be reacted with at least two phenol molecules, such as phenol molecule 346 and phenol molecule 348 with a protecting group (PG), to form cyclic phosphazene molecule 350. The at least two phenol molecules may include functional groups to functionalize the cyclic phosphazene molecule 345.

In various embodiments, cyclic phosphazene molecule 350 is then deprotected to form functionalized phosphazene molecule 355. In various embodiments, process 300-3 and process 300-2 illustrate identical reactions. In some embodiments, substituent R in process 300-3 is the third variable substituent R (FIG. 2).

Figure 3D:
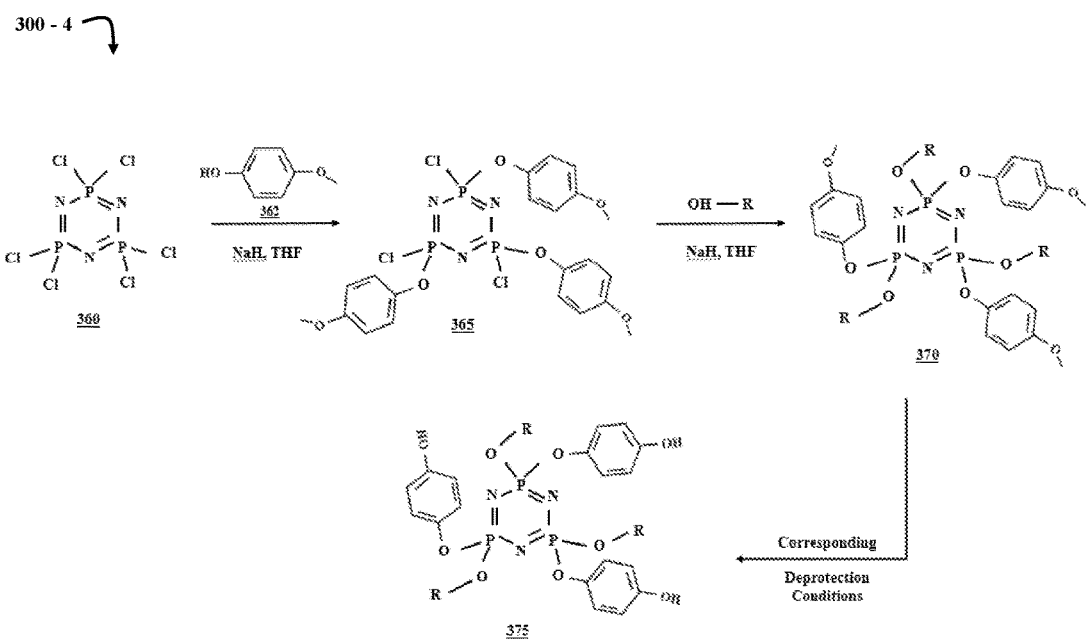
FIG. 3D depicts a fourth chemical reaction diagram illustrating a process of forming a cyclic phosphazene molecule, according to various embodiments.

Referring to FIG. 3D, a chemical reaction diagram illustrating a sample process 300-4 of forming a cyclic phosphazene molecule is depicted, according to various embodiments. In various embodiments, process 300-4 of forming a cyclic phosphazene molecule includes functionalizing a cyclic phosphazene molecule. Process 300-4 is one possible reaction for functionalizing a cyclic phosphazene molecule, and is illustrated for example purposes.

Process 300-4 begins with an exemplary cyclic phosphazene molecule 360. In some embodiments, cyclic phosphazene molecule 360 is an unfunctionalized cyclic phosphazene molecule. A strong base, such as sodium hydride (NaH), and tetrahydrofuran (THF) may be reacted with cyclic phosphazene molecule 360. In various embodiments, other bases (e.g., potassium hydride, lithium hydride, rubidium hydride, cesium hydride, etc.) or acids may be used in place of the strong base NaH. Additionally, a molecule such as phenol molecule 362 may be reacted with the cyclic phosphazene molecule 360, NaH, and THF to form cyclic phosphazene molecule 365. In various embodiments, the phenol molecule 362 includes functional groups to functionalize the unfunctionalized cyclic phosphazene molecule 360.

Cyclic phosphazene molecule 365 may then be reacted with NaH, THF, and an alcohol molecule to form cyclic phosphazene molecule 370. In various embodiments, the alcohol molecule may functionalize cyclic phosphazene molecule 365. Cyclic phosphazene molecule 370 may then be deprotected to form functionalized phosphazene molecule 375. In some embodiments, substituent R in process 300-4 is the third variable substituent R (FIG. 2). Substituent X in process 300-4 may be a protecting group such as a silyl group, THP, a benzyl group, a methoxymethyl acetal (MOM) group, and/or a methyl group.

Referring to FIG. 4, a schematic diagram of a flame-retardant microcapsule 400 with a shell containing cyclic phosphazene molecules is depicted, according to various embodiments. Microcapsule 400 includes cyclic phosphazene shell 410 and a core 420. The cyclic phosphazene shell 410 may be a shell containing cyclic phosphazene molecules and may contain additional molecules. In various embodiments, core 420 includes a payload agent. In some embodiments, flame-retardant microcapsule 400 is formed from the operations of process 100. Cyclic phosphazene shell 410 may have orthogonal functionalities and may bind into a polymeric matrix, as discussed herein.

In various embodiments, the flame-retardant microcapsule 400 with the shell containing cyclic phosphazene molecules is included in an article of manufacture. In some embodiments, the article of manufacture includes a material that contains the flame-retardant microcapsule 400. The material can be a resin, plastic, adhesive, or polymer. Examples of polymer materials can include polyurethane, epoxies, polyhydroxyurethane, polycarbonates, polyester, polyacrylates, polyimides, polyamides, polyureas, and poly(vinyl-ester). The article of manufacture may further include an electronic component.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. In some instances, reactions that involve multiple steps can be carried out sequentially, and, in other instances, they can be carried out in one pot. Further, in some embodiments, processes can be added or omitted while still remaining within the scope of the disclosure, as will be understood by a person of ordinary skill in the art.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A flame-retardant microcapsule with a shell containing a cyclic phosphazene molecule, the cyclic phosphazene molecule with a formula of:

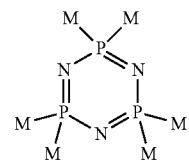

wherein each M is a first variable substituent.

2. The flame-retardant microcapsule of claim 1, wherein the M has a formula of:

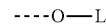

wherein L is a second variable substituent.

3. The flame-retardant microcapsule of claim 2, wherein the L is selected from the group consisting of substituents with formulas of:

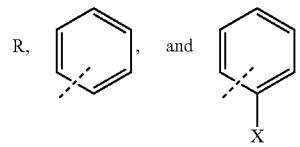

wherein R is a third variable substituent; and
wherein X is a fourth variable substituent.

4. The flame-retardant microcapsule of claim 3, wherein the R is a substituent comprising at least one of:
a hydrogen molecule, a vinyl group, an allyl group, an epoxy group, an acrylate group, a phenyl acrylic acid, and an acryloyl acid.

5. The flame-retardant microcapsule of claim 3, wherein the fourth variable substituent X is a substituent comprising at least one of:
the R, a hydroxide molecule, and an amidogen molecule.

6. The flame-retardant microcapsule of claim 1, wherein the cyclic phosphazene molecule has orthogonal functionality.

7. The flame-retardant microcapsule of claim 6, wherein the cyclic phosphazene molecule is covalently bonded into a polymeric matrix.

8. A process of forming a flame-retardant microcapsule with a shell containing a cyclic phosphazene molecule, comprising:
providing the cyclic phosphazene molecule;
forming an aqueous mixture containing the cyclic phosphazene molecule;
adding a payload agent into the aqueous mixture; and
adding a curing agent into the aqueous mixture.

9. The process of claim 8, wherein providing the cyclic phosphazene molecule includes functionalizing an unfunctionalized cyclic phosphazene molecule, wherein the cyclic phosphazene molecule is a functionalized cyclic phosphazene molecule.

10. The process of claim 9, wherein functionalizing the unfunctionalized cyclic phosphazene molecule is a reaction including at least one of functionalized aryl alcohols and functionalized aliphatic alcohols.

11. The process of claim 8, wherein the payload agent is a latent curing agent.

12. The process of claim 8, wherein the payload agent is selected from the group consisting of: cyclic olefins, norbornene, substituted norbornene, cyclooctadiene, substituted cyclooctadiene, lactones, acrylates, acrylic acids, styrenes, isoprene, butadiene, and epoxies.

13. The process of claim 8, further comprising:
adding one or more solvents into the aqueous mixture, the one or more solvents including at least one of aprotic solvents and protic solvents.

14. The process of claim 8, further comprising:
adding a cross-linking agent into the aqueous mixture to generate the shell around the payload agent.

15. The process of claim 8, wherein the cyclic phosphazene molecule has a formula of:

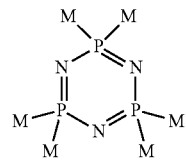

wherein each M is a first variable substituent.

16. The process of claim 15, wherein the M has a formula of:

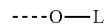

wherein L is a second variable substituent.

17. The process of claim 16, wherein the L is selected from the group consisting of substituents with formulas of:

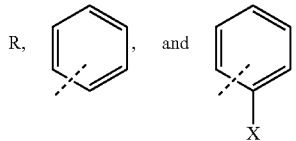

wherein R is a third variable substituent; and
wherein X is a fourth variable substituent.

18. An article of manufacture, comprising a flame-retardant microcapsule with a shell containing a cyclic phosphazene molecule.

19. The article of manufacture of claim 18, wherein the shell is covalently bound into a polymeric matrix.

20. The article of manufacture of claim 18, wherein the cyclic phosphazene molecule has a formula of:

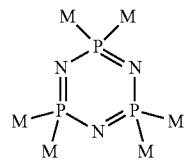

wherein each M is a first variable substituent.

* * * * *